(12) United States Patent
Baudisch et al.

(10) Patent No.: US 11,510,817 B2
(45) Date of Patent: Nov. 29, 2022

(54) HAPTIC DEVICE THAT ALLOWS BLIND USERS TO INTERACT IN REAL-TIME IN VIRTUAL WORLDS

(71) Applicant: Patrick Baudisch, Seattle, WA (US)

(72) Inventors: Patrick M Baudisch, Berlin (DE); Oliver Schneider, Waterloo (CA); Jotaro Shigeyama, Berlin (DE); Robert Kovacs, Berlin (DE)

( * ) Notice: Subject to any disclaimer, the term of this patent is extended or adjusted under 35 U.S.C. 154(b) by 70 days.

(21) Appl. No.: 16/755,020

(22) PCT Filed: Oct. 10, 2018

(86) PCT No.: PCT/US2018/055308
§ 371 (c)(1),
(2) Date: Apr. 9, 2020

(87) PCT Pub. No.: WO2019/075134
PCT Pub. Date: Apr. 18, 2019

(65) Prior Publication Data
US 2020/0345553 A1    Nov. 5, 2020

Related U.S. Application Data

(60) Provisional application No. 62/570,618, filed on Oct. 10, 2017.

(51) Int. Cl.
*A61F 9/08* (2006.01)
*G06F 3/01* (2006.01)
(Continued)

(52) U.S. Cl.
CPC ............... *A61F 9/08* (2013.01); *G06F 3/016* (2013.01); *G06F 3/0346* (2013.01);
(Continued)

(58) Field of Classification Search
CPC .... G06F 3/04815; G06F 3/011; G06F 3/0346; G06F 3/016; G06F 2203/015;
(Continued)

(56) References Cited

U.S. PATENT DOCUMENTS 5,186,629 A * 2/1993 Rohen ..................... G06F 3/016
340/4.12
6,184,847 B1 * 2/2001 Fateh ..................... G06F 3/011
345/8

(Continued)

FOREIGN PATENT DOCUMENTS

EP             3285144 A1 *  2/2018  ............. G06F 3/016

*Primary Examiner* — Vinh T Lam
(74) *Attorney, Agent, or Firm* — Edward B. Weller

(57) ABSTRACT

In some embodiments, a haptic device comprises first and second multi-dimensional spatial haptic devices. The first spatial haptic device includes a handle to represent a location of one object in a virtual document or space. The second spatial haptic device includes a handle to represent a location of another object in the same virtual document or space. The first and the second handles are spatially registered with respect to each other. In some embodiments, a third spatial haptic device includes a handle to represent a location of yet another object in a virtual document or space.

25 Claims, 9 Drawing Sheets

(51) Int. Cl.
   *G06F 3/0346* (2013.01)
   *G06F 3/0481* (2013.01)
   *G09B 21/00* (2006.01)
   *A63F 13/285* (2014.01)
   *A63F 13/812* (2014.01)
   *A63F 13/837* (2014.01)
   *G06F 3/04815* (2022.01)

(52) U.S. Cl.
   CPC ....... *G06F 3/04815* (2013.01); *G09B 21/004* (2013.01); *A63F 13/285* (2014.09); *A63F 13/812* (2014.09); *A63F 13/837* (2014.09); *A63F 2300/1037* (2013.01); *A63F 2300/8011* (2013.01); *A63F 2300/8076* (2013.01)

(58) Field of Classification Search
   CPC ....... G09B 21/003; G09B 21/004; A61F 9/08; G06K 9/00355; A63F 2300/8076; A63F 13/837; A63F 2300/8011; A63F 13/285; A63F 13/812; A63F 2300/1037
   See application file for complete search history.

(56) References Cited

U.S. PATENT DOCUMENTS

| | | | |
|---|---|---|---|
| 7,877,243 B2* | 1/2011 | Olien | A61B 34/74 703/3 |
| 9,703,381 B2* | 7/2017 | Gallo | A61B 34/74 |
| 10,463,978 B2* | 11/2019 | Tran | G09B 21/004 |
| 2004/0001734 A1* | 1/2004 | Burrell, IV | G09B 21/003 400/472 |
| 2004/0241623 A1* | 12/2004 | Lenay | G09B 21/001 434/112 |
| 2007/0247393 A1* | 10/2007 | Kuroki | G06T 1/00 345/8 |
| 2017/0108930 A1* | 4/2017 | Banerjee | A61B 90/37 |
| 2017/0329510 A1* | 11/2017 | Gorlich | G09B 21/008 |
| 2018/0001192 A1* | 1/2018 | Vaughn | A63F 13/285 |
| 2018/0039404 A1* | 2/2018 | MacIsaac | G06F 3/04886 |
| 2019/0101994 A1* | 4/2019 | Kira | G06F 3/0383 |
| 2020/0233484 A1* | 7/2020 | Thayer | G06F 3/016 |

* cited by examiner

HAPTIC DEVICE THAT ALLOWS BLIND USERS TO INTERACT IN REAL-TIME IN VIRTUAL WORLDS

RELATED APPLICATION

This application claims the benefit under 35 USC § 119 to U.S. Provisional Patent Application Ser. No. 62/570,618 filed on Oct. 10, 2017, which is incorporated by reference herein in its entirety.

BACKGROUND

Unless otherwise indicated herein, the approaches described in this section are not admitted to be prior art by inclusion in this section Today, users unable to see visual output on a computer screen (aka blind users) already operate a wide range of computer applications, from dynamic text documents [HyperBraille, http://www.hyperbraille.de/] to games [Tony Morelli, John Foley, Luis Columna, Lauren Lieberman, and Eelke Folmer. VI-Tennis: a vibrotactile/audio exergame for players who are visually impaired." In *Proceedings of the Fifth International Conference on the Foundations of Digital Games*, pp. 147-154. *ACM*, 2010. DOI:http://dx.doi.org/10.1145/1822348.1822368]. Spatial applications are also available through novel interfaces, including tactile maps [Peter Parente, and Gary Bishop. 2003. BATS: the blind audio tactile mapping system. In *Proceedings of the ACM Southeast regional conference*, pp. 132-137.], mobile way finding devices [David A. Ross, and Bruce B. Blasch. 2000. Wearable interfaces for orientation and wayfinding. In *Proceedings of the fourth international ACM conference on Assistive technologies*, pp. 193-200. DOI: https://doi.org/10.1145/354324.354380], and graphics displayed through touch [Polly Edman. Tactile graphics. *American Foundation for the Blind*, 1992., S. Paneels and J. C. Roberts. 2010. Review of Designs for Haptic Data Visualization. in *IEEE Transactions on Haptics*, vol. 3, no. 2, pp. 119-137. DOI: https://doi.org/10.1109/TOH.2009.44].

However, there are no systems yet that would allow blind users to interact with moving objects in virtual worlds, as would be necessary to play sports games or shooter games. This class of applications is particularly challenging because it requires users to have a notion of a virtual space and to be able to track objects in the represented world, such as the player's opponents or a soccer ball.

Spatial environments without motion are well studied. Raised lines created using swell paper [Swell-form-graphics: http://www.americanthermoform.com/product/swell-form-graphics-ii-machine/] or 3D printers [Saiganesh Swaminathan, Thijs Roumen, Robert Kovacs, David Stangl, Stefanie Mueller, and Patrick Baudisch. 2016. Linespace: A Sensemaking Platform for the Blind. In *Proceedings of the 2016 CHI Conference on Human Factors in Computing Systems* (CHI '16). ACM, New York, N.Y., USA, 2175-2185. DOI: https://doi.org/10.1145/2858036.2858245] and Braille arrays [HyperBraille, http://www.hyperbraille.de/] allow creating dot and line drawings. The same strategy applies to spatial documents displayed using a force-feedback system, which users explore by scanning using an end effector [S. Paneels and J. C. Roberts. 2010. Review of Designs for Haptic Data Visualization. in *IEEE Transactions on Haptics*, vol. 3, no. 2, pp. 119-137. DOI: https://doi.org/10.1109/TOH.2009.44].

Unfortunately, blind users cannot perceive such spatial displays all at once, but must "scan" the space sequentially by running their fingers across it [Susan J Lederman, Roberta L Klatzky, Hand movements: A window into haptic object recognition, In *Cognitive Psychology*, Volume 19, Issue 3, 1987, Pages 342-368, ISSN 0010-0285, DOI:https://doi.org/10.1016/0010-0285(87)90008-9]. If anything changes or moves in such a display, blind users will not become aware of the change until they reach this object during the next scan. This makes it impossible to track moving objects, such as soccer balls or opponents, and essentially limits the interaction to turn-taking.

To inform users about a moving object, researchers proposed adding a vibrotactile actuator that indicates the distance to a ball (e.g., [Beryl Plimmer, Andrew Crossan, Stephen A. Brewster, and Rachel Blagojevic. 2008. Multimodal collaborative handwriting training for visually-impaired people. In *Proceedings of the SIGCHI Conference on Human Factors in Computing Systems* (CHI '08). ACM, New York, N.Y., USA, 393-402. DOI: https://doi.org/10.1145/1357054.1357119]). Similarly, audio pitch and audio volume can provide coarse information about an object's distance [Audio Game Hub. http://www.audiogamehub.com]. But, how can a system indicate the location of a moving object?

SUMMARY

In this disclosure, a different approach is presented. Two force-feedback devices are combined in a spatially registered arrangement, such as two haptic pantograph. The resulting device, DualPanto, allows users to experience the spatial relationship between the user's avatar and other objects in the virtual world.

The disclosure presents a new haptic device that enables blind users to interact with spatial virtual environments that contain objects moving in real-time, as is the case in sports or shooter games. Users interact with DualPanto by operating its me handle with one hand and by holding on to its it handle with the other hand. Each handle is connected to a 2D haptic input/output device, such as a haptic pantograph (such as the device described in "The Pantograph Mk-II: A Haptic Instrument" by Gianni Campion and Vincent Hayward, in Proc. IROS 2005, IEEE/RSJ Int. Conf. Intelligent Robots and Systems, pp. 723-728.), a robotic arm, a force feedback device (such as a Phantom, a Novinth Falcon, etc.), a gantry, or similar. A feature is that the two handles are spatially registered with respect to each other. When guiding their avatar through a virtual world using the me handle, spatial registration enables users to track moving objects by allowing the it handle to guide the hand holding it. The registration between both handles allows blind players of a shooter game, for example, to aim at an opponent or dodge the opponent's shots; it allows blind players of a 1-on-1 soccer game to race for the ball or evade an opponent.

DETAILED DESCRIPTION

Dualpanto

DualPanto is a haptic device that enables blind users to interact with spatial 2D documents or virtual environments, including those that contain moving objects.

FIG. 1a shows a blind user using our prototype device called DualPanto to play a first-person shooter [Survival Shooter Tutorial "Zombunny", Unity Asset store. https:// www.assetstore.unity3d.com/en/#!/content/40756]—a shooter designed for sighted users.

As shown in FIG. 1b, the device features two handles. Users interact with DualPanto by operating the me handle with one hand and by holding on to the it handle with the other. DualPanto applications generally use the me handle to represent the user's avatar in the virtual world and the it handle to represent some other potentially moving entity, such as the opponent in a shooter game. (A user handle is referred to herein as a me handle and is a handle that receives movement input and in some embodiments also rotation and other input from a user. An object handle is referred to herein as an it handle, and is a handle that provides forces, and torques to the user to indicate movement, rotation, existence, or other output to a user based on an object in the virtual space.) In other embodiments, the haptic device includes more than two handles, such as those described below.

Note that we understand the term avatar broadly, i.e., while it could refer to a literal representation of the user in the virtual world, it may also refer to a very abstract representation of the user, such as "a location currently influenced by the user."

Figure 2:
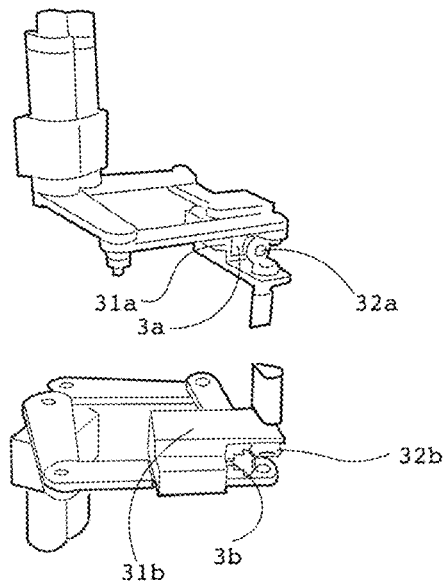
FIG. 2 shows the mechanics behind DualPanto.

FIG. 2 shows the mechanics behind DualPanto. (a) For this particular embodiment, the me handle and the it handle are attached to one haptic input/output positioning device each (here a variation of the device described in "The Pantograph Mk-II: A Haptic Instrument" by Gianni Campion and Vincent Hayward, in Proc. IROS 2005, IEEE/RSJ Int. Conf. Intelligent Robots and Systems, pp. 723-728, combined with an additional rotary haptic handle attached to the end effector each one of them). The handles are motorized rotary knobs with encoders that allows them act as input and output. This setup allows each of the two handles to move in their own horizontal plane and to rotate, so that each hand interacts with three degrees of freedom.

Each pantograph device provides force feedback with the help of the two motors driving the pantograph and the third motor driving the knob. Each pantograph device senses its current position and orientation with the help of three encoders: one attached to each of the two pantograph motors and one attached to the knob.

There are several ways of implementing the 2D haptic input/output device, such as using a haptic pantograph (such as the device described in "The Pantograph Mk-II: A Haptic Instrument" by Gianni Campion and Vincent Hayward, in Proc. IROS 2005, IEEE/RSJ Int. Conf. Intelligent Robots and Systems, pp. 723-728.), a robotic arm, a force feedback device (such as a Phantom, a Novinth Falcon, etc.), a gantry mechanism, or similar, as we discuss in additional detail later in this disclosure. In this disclosure, we will use the term haptic pantograph or just pantograph for short, to refer to refer to this wider set of embodiments.

Interacting with DualPanto

Figure 3:
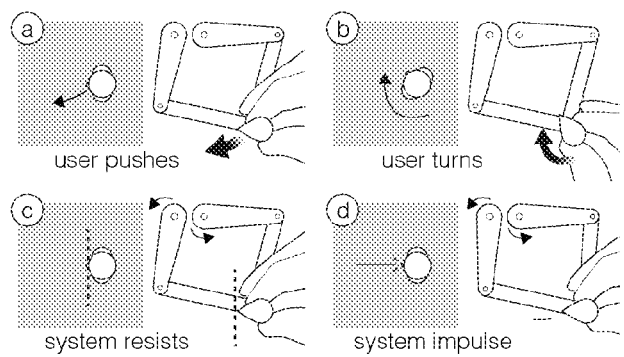
FIG. 3a is a diagram illustrating movement of an avatar in response to movement of a me handle according to one embodiment. The me handle allows users to move.
FIG. 3b is a diagram illustrating rotation of an avatar in response to rotation of a me handle according to one embodiment.
FIG. 3c is a diagram illustrating a movement of an avatar into a wall in response to movement of a me handle according to one embodiment.
FIG. 3d is a diagram illustrating a movement of an avatar with force feedback in response to movement of a me handle according to one embodiment (impact using force feedback).

To allow users to understand the spatial relationship between the user's avatar and another virtual entity in real-time, DualPanto operates as follows:

Me handle: As shown in FIG. 3, DualPanto's applications generally use the me handle to represent the user's avatar in the virtual world. In some embodiments, users operate the me handle using their dominant hand; other embodiments may let users use their non-dominant hand or other part of their body. (a) Users move around and explore the virtual environment by moving the me handle. The device typically uses a direct 1:1 mapping (i.e., similar to the mapping of a touch screen), so that returning the handle to the same location in the physical world returns the avatar to same location in the virtual world. (b) The knob itself allows users to rotate their avatar. (c) The me handle renders walls e.g., by applying the god-object haptic rendering algorithm [C. B. Zilles, and J. K. Salisbury. 1995. A constraint-based god-object method for haptic display. In *Proceedings* 1995 *IEEE/RSJ International Conference on Intelligent Robots and Systems. Human Robot Interaction and Cooperative Robots*,Vol. 3, pp. 146-151. DOI:http://doi.org/10.1109/IROS.1995.525876]. (d) Furthermore, it may provide additional output, such as play back impulse sequences when, for example, the player is hit by a projectile.

Figure 4:
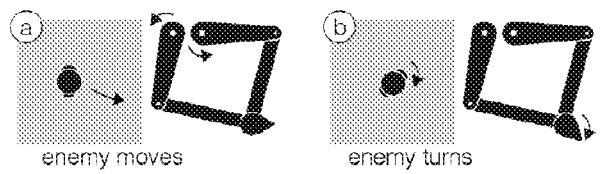
FIGS. 4a and 4b are diagrams illustrating it handles used to track movement and rotation, respectively, of an object according to one embodiment. (a) The enemy moves along the shown arrow. Users track an object by allowing their hand to be guided by the it handle. (b) users track how the enemy turns, as shown using the arrow, by allowing their hand to be rotated by its knob.

It handle: As shown in FIG. 4, DualPanto applications use the it handle to render one selected moving object, such as the opponent in a first-person shooter. Users generally operate it using their non-dominant hand, but can operate either handle with either hand, and even switch hands during operation. (a) If the object represented by the it handle moves, so does the handle. The handle is typically actuated only by the device, i.e., it will resist users trying to move it. By letting the it handle guide their hand, users can track the associated object, i.e., feel how it moves and obtain a sense of where it is currently located with respect to user's avatar. (b) At the same time, the actuated knob conveys to the user what direction it is facing. The it handle may also display a number of haptic icons, such as a wiggle, when the represented opponent is shot. Other actuation mechanisms, such as vibro tactile actuators, or motors supporting additional directions or movement may be attached as well.

Note how the it handle is substantially different from the me handle. While both allow users to learn about objects in the virtual world, say an opponent, they do so in very different ways. Using the me handle users may try to trace the outside of an object. If they do so long enough, they will be able to describe the object with a certain level of detail. Along they way, users can try to conclude certain higher-level properties of the object, such as the location of its center. This approach is slow and a side effect is that the object may move before the exploration is complete. In this case, the contours may appear distorted to the user. The user may also lose track of the object and so on.

In contrast, when users perceive the same object by means of the it handle, they perceive only a highly reduced version of the object, such as its center of mass and the orientation of the represented players nose. This highly reduced information, however, can now be conveyed instantaneously, so it is very fast. Observation over time also does not cause shape and motion to interfere; instead the it handle clearly displays the position of the object over time. And as long as users physically hold on to the handle, they will never lose track of the virtual object it represents. These properties of the it handle enable real-time applications not previously possible.

Figure 5:
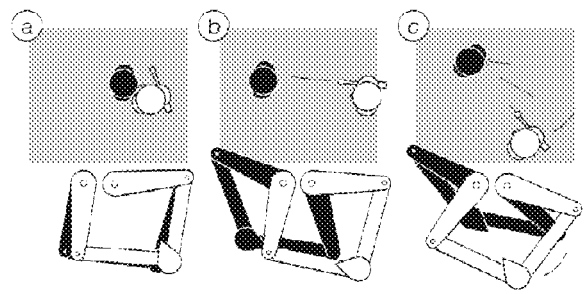
FIGS. 5a, 5b, and 5c are diagrams illustrating a me handle and an it handle used in a zombie game according to one embodiment. The me handle (white) and the it handle (black) are spatially registered. This allows users to interact in real-time. (a) When a zombie approaches the player, the user can (b) dodge while starting to take aim. (c) After aiming at the zombie, the player shoots.

Registration: The key feature behind DualPanto is that the me handle and the it handle are spatially registered with respect to each other, as illustrated by FIG. 5. (a) For example, if the me handle is located directly above the it handle, the user knows that the user's avatar has collided with the opponent in the virtual world. In a shooter game, for example, this would typically indicate that the player is being attacked in hand-to-hand combat. (b) Spatial registration allows users to know where it is relative to me. In a shooter game this allows aiming and shooting at an opponent. (c) Similarly, feeling the position and orientation of the opponent allows users to evade the opponent's shots, e.g., by moving sideways while shooting (aka strafing).

Figure 6:
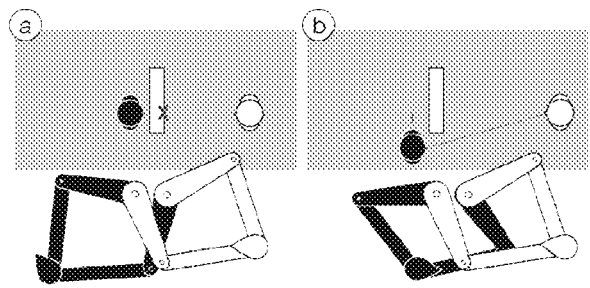
FIGS. 6a and 6b are diagrams illustrating an it handle in a non-visible object and a visible object situations, respectively, according to one embodiment. (a) When it is not visible to the user, the it handle relaxes. (b) When it enters the user's line of sight again, the handle reengages.

Hiding: As shown in FIG. 6, it may not be visible to the user. (a) Some embodiments may convey this to the user by relaxing the it handle, i.e., while it stays where it is, the motors driving this handle are turned off, allowing the user to back-drive the handle. (b) When it enters the user's line of sight again, the motors engage again and snap the it handle to its position.

Figure 7:
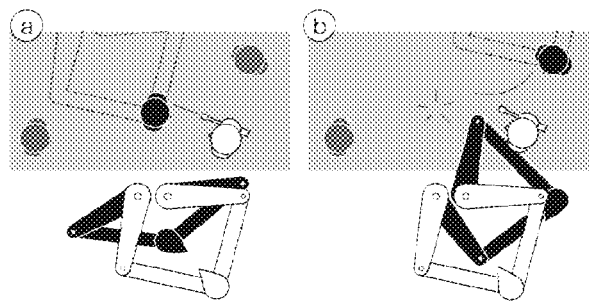
FIGS. 7a and 7b are diagrams illustrating positions of handles and multiplexing multiple avatars in a shooting game according to one embodiment. (a) The closest enemy is displayed on the it handle so that the user can take aim and shoot. If this opponent goes down, (b) the it handle swings to the next closest opponent.

Multiplexing it: When the virtual scene contains multiple relevant objects, the it handle may multiplex between them. FIG. 7 shows an example for a shooter game. (a) Here it may always represent the closest opponent. If the opponent goes down, (b) the it handle automatically snaps to the next opponent. Other embodiments may employ different algorithms for determining which object it refers to, such as time multiplexing, explicit control by the user, etc.

Applications

Conceptually, a wide range of application for blind users can benefit from DualPanto, in particular any application that revolves around the spatial relationship between two or more entities, such as drawing curves with digital tape sketching [Ravin Balakrishnan, George Fitzmaurice, Gordon Kurtenbach, and William Buxton. 1999. Digital tape drawing. In *Proceedings of the 12th annual ACM symposium on User interface software and technology (UIST '99). ACM*, New York, N.Y., USA, 161-169. DOI:http://dx.doi.org/10.1145/320719.322598] or a dynamic home finder application [Christopher Williamson and Ben Shneiderman 1992. The dynamic HomeFinder: evaluating dynamic queries in a real-estate information exploration system. In Proceedings of the 15th annual international ACM SIGIR conference on Research and development in information retrieval (SIGIR '92). ACM, New York, N.Y., USA, 338-346. DOI: https://doi.org/10.1145/133160.133216] that can guide users along routes and towards available apartments, 2D and 3D editing, retouching images, spatial games, etc. However, DualPanto's ability to render objects moving in real time makes it particularly suited for applications that represent a virtual world and this certainly includes real-time spatial games. To illustrate this we implemented two example games.

Figure 1:
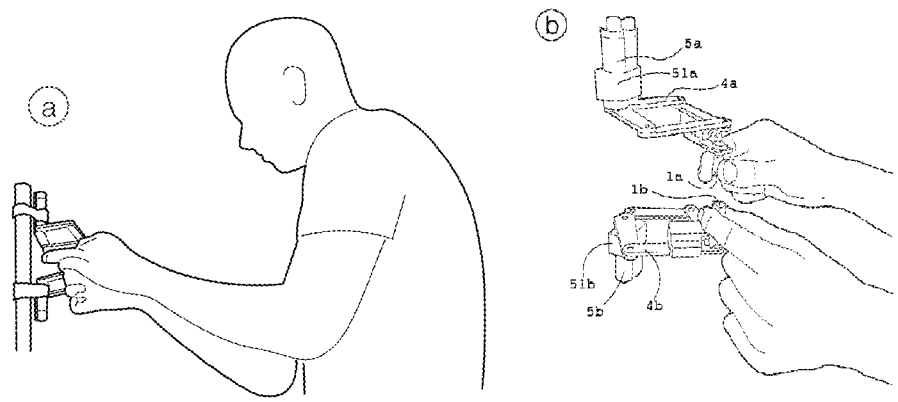
FIG. 1a is a diagram illustrating a haptics device according to one embodiment. This blind user is playing a first-person shooter designed for sighted users.
FIG. 1b is a diagram illustrating a me handle and an it handle of the haptics device of FIG. 1a according to one embodiment. The DualPanto bimanual force feedback device enables this. Its me handle 1a allows users to move their avatar around the virtual space. Force feedback prevents users from crossing virtual walls, driven by two motors 5a fixed with a bracket 51a, connected to linkages 4a to render force. The it handle 1b moves by itself. It allows users to feel where the current opponent is located and what direction it faces. This handle is also driven by two motors 5b fixed with a bracket 51b, connected to linkages 4b. Users aim using the haptic knob on the me handle; a foot pedal fires the gun.

Shooter is a first-person survival shooter game already shown in FIG. 1. In this game (based on Survival Shooter Tutorial "Zombunny", Unity Asset store. https://www.assetstore.unity3d.com/en/#!/content/40756) the player must fight a horde of zombie bunnies by avoiding their touch and shooting at each zombie as it approaches. FIG. 3 through FIG. 7 give examples of the interaction design behind this program.

Figure 8:
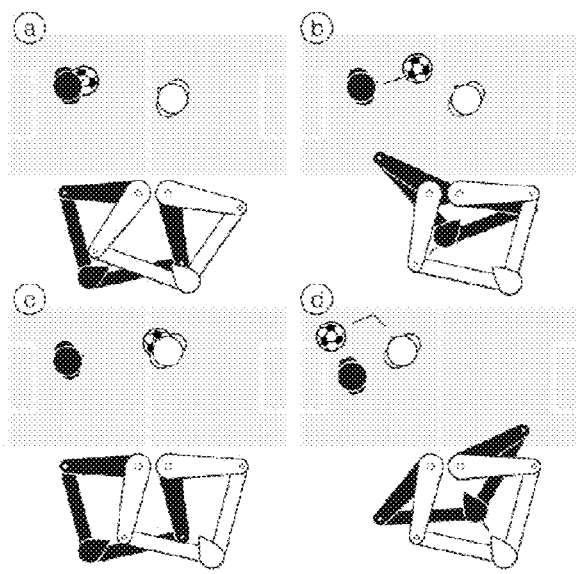
FIGS. 8a, 8b, 8c, and 8d are diagrams illustrating positions of handles and avatars in a soccer game according to one embodiment. Walkthrough of dualPanto soccer game. (a) The me handle shows the position of the player, and the it handle shows the position of opponent player with a ball. (b) The opponent kicks the ball and then the it handle switches to show the position of the ball in the soccer field. (c) The player approaches and catches the ball. The it handle then shows the position of the opponent. (d) The player kicks the ball to the direction of the me handle, and the it handle now shows the position of the ball again.

1:1 Soccer is our two-player game we implemented. FIG. 8 shows an example interaction. (a) The opponent has the ball, so the player pays attention to which way they are looking. (b) The opponent shoots the ball; the it handle now follows the soccer ball as it moves. (c) Knowing where the ball is going, the player run towards the ball and intercepts it. The player catches the ball and now it snaps to the opponent. (d) The player notices an opening and scores a goal by rebounding off the wall.

Figure 9:
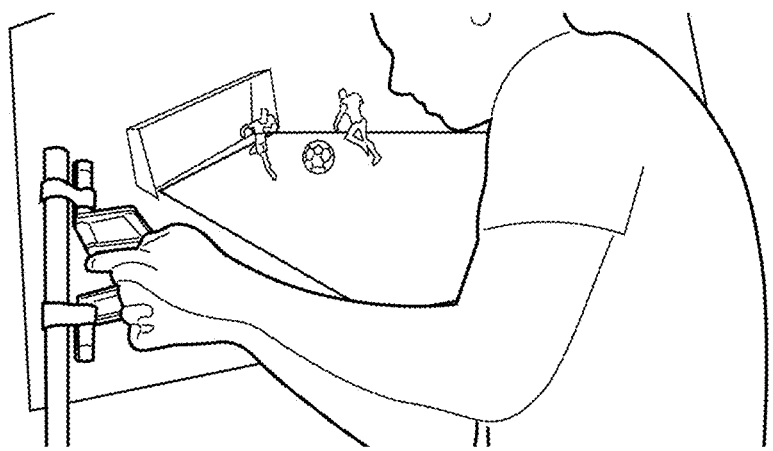
FIG. 9 is a diagram illustrating a haptic device uses for a soccer game according to one embodiment. This is a blind user playing 1:1 soccer (here against a sighted opponent).

In FIG. 9, we show a blind player playing the blue avatar performing the maneuver from FIG. 8*d*.

Contributions & Limitations

Our main contribution is a new haptic device that enables blind users to interact with spatial virtual environment that contain moving objects, as is the case in sports games or first person shooters.

DualPanto accomplishes this by combining two paradigms of haptic feedback: an explored virtual environment for player-centric information, and a passively displayed stream of spatial information for tracked objects. The registration between the two is key. As we demonstrated in our walkthrough, this allows for various types of interaction including spatial navigation, locating and tracking of virtual objects, dodging, hiding, and aiming.

Related Work

Our work builds on previous work in haptic environments, haptic display of streamed spatial data, and co-registered environments, especially for blind and visually impaired users.

Haptic Feedback for Exploring Virtual Environments

Haptic displays for blind and visually impaired users have traditionally focused on four main categories areas: Braille displays, tactile or haptic graphics, guidance and wayfinding, and sensory substitution [Dianne T V Pawluk, Richard J. Adams, and Ryo Kitada. 2015. Designing haptic assistive technology for individuals who are blind or visually impaired. *IEEE transactions on haptics* 8, no. 3: 258-278. DOI:https://doi.org/10.1109/TOH.2015.2471300]. Of these, Braille displays and tactile and haptic graphics are able to render virtual environments.

Virtual environments can be rendered for the tactile sense, i.e., sensed with the skin so that the point of connection is the user's finger and hands on a tactile display. Tactile graphics [Polly Edman. Tactile graphics. *American Foundation for the Blind*, 1992.] are two-dimensional tactile renditions of information. Common static versions include raised graphics on Swell paper [Swell-form-graphics: http://www.americanthermoform.com/product/swell-form-graphics-ii-machine/], buckled lines [Raised Line Drawing Kits: http://www.maxiaids.com/raised-line-drawing-kit], or thermoform shapes produced by vacuum [Polly Edman. Tactile graphics. *American Foundation for the Blind*, 1992.].

Dynamic versions have been rendered with haptic devices like skin-stretch actuators on a pantograph mechanism [Grégory Petit, Aude Dufresne, Vincent Levesque, Vincent Hayward, and Nicole Trudeau. 2008. Refreshable tactile graphics applied to schoolbook illustrations for students with visual impairment. In *Proceedings of the 10th international ACM SIGACCESS conference on Computers and accessibility* (Assets '08). ACM, New York, N.Y., USA, 89-96. DOI:https://doi.org/10.1145/1414471.1414489], large Braille pin displays [HyperBraille, http://www.hyperbraille.de/], or even larger 3-D printed lines [Saiganesh Swaminathan, Thijs Roumen, Robert Kovacs, David Stangl, Stefanie Mueller, and Patrick Baudisch. 2016. Linespace: A Sensemaking Platform for the Blind. In *Proceedings of the 2016 CHI Conference on Human Factors in Computing Systems* (CHI '16). ACM, New York, N.Y., USA, 2175-2185. DOI: https://doi.org/10.1145/2858036.2858245]. Surface haptics involves tactile rending on surfaces, e.g., with programmable friction [Olivier Bau, Ivan Poupyrev, Ali Israr, and Chris Harrison. 2010. TeslaTouch: electrovibration for touch surfaces. In *Proceedings of the 23nd annual ACM symposium on User interface software and technology* (UIST '10). ACM, New York, N.Y., USA, 283-292. DOI: https://doi.org/10.1145/1866029.1866074,L. Winfield, J. Glassmire, J. E. Colgate and M. Peshkin. 2007. T-PaD: Tactile Pattern Display through Variable Friction Reduction, *Second Joint EuroHaptics Conference and Symposium on Haptic Interfaces for Virtual Environment and Teleoperator*

Systems (WHC'07), Tsukaba, pp. 421-426. DOI:https://doi.org/10.1109/WHC.2007.105].

Virtual environments rendered with force feedback involve one or more end effector(s). For blind users, spatial data can be represented by means of haptification [S. Paneels and J. C. Roberts. 2010. Review of Designs for Haptic Data Visualization. in *IEEE Transactions on Haptics*, vol. 3, no. 2, pp. 119-137. DOI: https://doi.org/10.1109/TOH.2009.44], for example force-feedback line graphs, where their hands are guided along a line as they move along it [Mikro Horstmann, Cornelius Hagen, Alisdair King, Sijo Dijkstra, David Crombie, David Gareth Evans, George T. Ioannidis, Paul Blenkhorn, Otthein Herzog, and Christoph Schlieder. 2004. "TeDUB: Automatic interpretation and presentation of technical diagrams for blind people." In *Proceedings of Conference and Workshop on Assistive Technologies for Vision and Hearing Impairment-CVHI'2004, EURO-ASSIST-VHI-2: Accessibility, Mobility and Social Integration*.].

Gaming environments for blind and visually impaired users are dominated by Audio Games [Audio Games. https://www.audiogames.net]. Spatial environments rely on left or right audio cues, or on mappings of location to pitch or volume [Audio Game Hub. http://www.audiogamehub.com]. While voice interaction can involve spatial or postural information, for example, with eyes-free yoga [Kyle Rector, Cynthia L. Bennett, and Julie A. Kientz. 2013. Eyes-free yoga: an exergame using depth cameras for blind & low vision exercise. In *Proceedings of the 15th International ACM SIGACCESS Conference on Computers and Accessibility* (ASSETS '13). New York, N.Y., USA, DOI: http://dx.doi.org/10.1145/2513383.2513392], most spatial interaction is limited. Vibrating tactile cues can provide additional information, for example, timing in a tennis game [Tony Morelli, John Foley, Luis Columna, Lauren Lieberman, and Eelke Folmer. VI-Tennis: a vibrotactile/audio exergame for players who are visually impaired." In *Proceedings of the Fifth International Conference on the Foundations of Digital Games*, pp. 147-154. ACM, 2010. DOI: http://dx.doi.org/10.1145/1822348.1822368], or location of non-moving objects (bowling pins) by scanning with a Wiimote in a bowling game [Tony Morelli, John Foley, and Eelke Folmer. 2010. Vi-bowling: a tactile spatial exergame for individuals with visual impairments. In *Proceedings of the 12th international ACM SIGACCESS conference on Computers and accessibility* (ASSETS '10), New York, N.Y., USA, 179-186. DOI:http://dx.doi.org/10.1145/1878803.1878836]. Moving objects have been approximated with vibration, e.g., with a vibrating pong paddle [Steven Strachan, Wiertlewski, M., Zophoniasson, H., & Anastassova, M. 2013. ViPong: Probabilistic haptic feedback for eyes-free interaction. In *IEEE World Haptics Conference* (WHC). pp. 193-198. DOI:https://doi.org/10.1109/WHC.2013.6548407].

Streamed Spatial Information

An alternative to explored haptic environments, haptic systems can stream spatial information to users as output only. For example, work on haptic icons [Karon MacLean and Mario Enriquez. 2003. Perceptual design of haptic icons. In *Proceedings of EuroHaptics*, pp. 351-363.] found that space is a major design parameter [Eric Gunther and Sile O'Modhrain. 2003.Cutaneous grooves: composing for the sense of touch. *Journal of New Music Research* 32, no. 4: 369-381.]. Grids of vibrotactile actuators can produce the motion with of phantom sensations and apparent motion [Ali Israr and Ivan Poupyrev. 2011. Tactile brush: drawing on skin with a tactile grid display. In *Proceedings of the SIGCHI Conference on Human Factors in Computing Systems* (CHI '11), New York, N.Y., USA, 2019-2028. DOI: https://doi.org/10.1145/1978942.1979235] across actuators; this can be streamed in real-time [Oliver S. Schneider, Ali Israr, and Karon E. MacLean. 2015. Tactile Animation by Direct Manipulation of Grid Displays. In Proceedings of the 28th Annual ACM Symposium on User Interface Software & Technology (UIST '15). ACM, New York, N.Y., USA, 21-30. DOI: https://doi.org/10.1145/2807442.2807470]. Skin-drag displays [Alexandra Ion, Edward Jay Wang, and Patrick Baudisch. 2015. Skin Drag Displays: Dragging a Physical Tactor across the User's Skin Produces a Stronger Tactile Stimulus than Vibrotactile. In *Proceedings of the 33rd Annual ACM Conference on Human Factors in Computing Systems* (CHI '15), New York, N.Y., USA, 2501-2504. DOI: https://doi.org/10.1145/2702123.2702459] directly move a tactor across the skin for more salient motion.

Proprioception can also stream spatial information for users using motion guidance. Originally a technique for teaching motor skills like golf swings [Yasuyoshi Yokokohji, Ralph L. Hollis, Takeo Kanade, Kazuyuki Henmi, and Tsuneo Yoshikawa. 1996. Toward machine mediated training of motor skills. Skill transfer from human to human via virtual environment. In *5th IEEE International Workshop on Robot and Human Communication*. pp. 32-37. DOI: https://doi.org/10.1109/ROMAN.1996.568646], motion guidance can also be display information. Gesture output [Anne Roudaut, Andreas Rau, Christoph Sterz, Max Plauth, Pedro Lopes, and Patrick Baudisch. 2013. Gesture output: eyes-free output using a force feedback touch surface. In *Proceedings of the SIGCHI Conference on Human Factors in Computing Systems* (CHI '13). ACM, New York, N.Y., USA, 2547-2556. DOI: https://doi.org/10.1145/2470654.2481352] moves a user's fingers to display gestures. Muscle Plotter [Pedro Lopes, Doǎa Yüksel, François Guimbretière, and Patrick Baudisch. 2016. Muscle-plotter: An Interactive System based on Electrical Muscle Stimulation that Produces Spatial Output. In *Proceedings of the 29th Annual Symposium on User Interface Software and Technology* (UIST '16). ACM, New York, N.Y., USA, 207-217. DOI: https://doi.org/10.1145/2984511.2984530] uses electrical muscle stimulation to actuate users' arms to plot graphs. Lopes et al. also envisioned a proprioceptive hand-slap game, where one hand is actuated by the user and the other by the system using electrical muscle stimulation [Pedro Lopes, Alexandra Ion, Willi Mueller, Daniel Hoffmann, Patrik Jonell, and Patrick Baudisch. 2015. Proprioceptive Interaction. In *Proceedings of the 33rd Annual ACM Conference on Human Factors in Computing Systems* (CHI '15), New York, N.Y., USA, 939-948. DOI: https://doi.org/10.1145/2702123.2702461].

Motion guidance has been used to help blind users navigate with an actuated cane [Johann Borenstein, and Iwan Ulrich. 1997. The guide cane—a computerized travel aid for the active guidance of blind pedestrians. In IEEE *International Conference on Robotics and Automation*, vol. 2, pp. 1283-1288. DOI:https://doi.org/10.1109/ROBOT.1997.614314]. More recently, the McSig system helped to teach handwriting to blind students through both trajectory replay and real-time demonstration by a teacher [Beryl Plimmer, Andrew Crossan, Stephen A. Brewster, and Rachel Blagojevic. 2008. Multimodal collaborative handwriting training for visually-impaired people. In *Proceedings of the SIGCHI Conference on Human Factors in Computing Systems* (CHI '08). ACM, New York, N.Y., USA, 393-402. DOI: https://doi.org/10.1145/1357054.1357119].

Unlike streamed spatial display, DualPanto enables users to act within the same environment as the display.

Registered Input and Output

DualPanto uses a single registered workspace for locating both hands in the same space. Displays like LucidTouch [Daniel Wigdor, Clifton Forlines, Patrick Baudisch, John Barnwell, and Chia Shen. 2007. Lucid touch: a see-through mobile device. In *Proceedings of the 20th annual ACM symposium on User interface software and technology* (UIST '07). ACM, New York, N.Y., USA, 269-278. DOI: https://doi.org/10.1145/1294211.1294259] have done this for a visual touchscreen device having interaction both in front of and behind a mobile device. Bimanual haptic interfaces often allow both hands to act in a virtual environment, such as surgery training simulators [Anthony Talvas, Maud Marchal, and Anatole Lécuyer. 2014. A survey on bimanual haptic interaction. *IEEE transactions on haptics* 7, no. 3: 285-300. DOI: https://doi.org/10.1109/TOH.2014.2314456]. However, each hand in these environments represents exactly the user's hands or implements. In DualPanto, in contrast, each hand corresponds to a different virtual object, and the user only acts in the virtual environment with the me hand.

Implementation

To allow readers replicate our work, we describe the details of our implementation here.

Pantographs

One set of embodiments is based on the haptic pantograph design, because it is planar and appropriate for a single registered workspace while naturally avoiding collisions between the handles.

Embodiments based on the haptic pantographs may be implemented using a variety of designs. For high-precision, someone skilled in the art may choose a design similar to the original haptic pantograph [Campion, G. 2005. The pantograph MK-II: a haptic instrument. In *The Synthesis of Three Dimensional Haptic Textures: Geometry, Control, and Psychophysics* (pp. 45-58). Springer London.] or "The Pantograph Mk-II: A Haptic Instrument" by Gianni Campion and Vincent Hayward, in Proc. IROS 2005, IEEE/RSJ Int. Conf. Intelligent Robots and Systems, pp. 723-728.), which achieves high precision using a motor in a direct drive setup and a very high-resolution encoder.

The embodiment shown so far implements a lower-cost variation of this design, inspired by the open-source Haply platform [Colin Gallacher, Arash Mohtat, Steve Ding, and József Kövecses. 2016. Toward open-source portable haptic displays with visual-force-tactile feedback colocation. In *Haptics Symposium* (HAPTICS), pp. 65-71. DOI:https://doi.org/10.1109/HAPTICS.2016.7463157]. The pantographs in the embodiment illustrated in FIG. 2 contain two DC motors each (Portescap, 12V) with attached 27:1 gearheads and optical encoders. We chose the motors and gear ratio carefully to be able to overpower user's hand when rendering an opponent's position or a wall, but still to allow users to back-drive the motors when using it in input mode. Other embodiments may choose different motors and transmission ratios (we also used high-end Maxon motors and low-cost Mabuchi motors).

Slack/Backlash

As common in haptic devices, slack at the end effector can affect the user's experience. To minimize slack, some embodiments use direct drive with a strong motor (as described, for example, in "The Pantograph Mk-II: A Haptic Instrument" by Gianni Campion and Vincent Hayward, in Proc. IROS 2005, IEEE/RSJ Int. Conf. Intelligent Robots and Systems, pp. 723-728.), which tends to offer very good results. In order to produce a cheaper version of this device, the high-resolution encoder may be replaced with a low-resolution and thus cheaper encoder coupled to the motor axle or linkage using a no-slack/low-slack mechanism that gears the motor rotation up before hitting the encoder.

Some embodiments may choose to use weaker motors with gearboxes instead. To keep slack under control, the gearbox could be a low-slack gearbox instead or any other low-slack transmission. Suitable technologies include, but are not limited to low-backlash gearboxes, capstan drives, no-backlash gear systems, such as the Archimedes drive (https://imsystems.nl/the-technology), harmonic drives, friction drives, etc. These embodiments can also work with low-resolution encoders driven directly by the motor.

Handles

Some embodiments offer motorized me and it handles. These are mounted to the end effector of the pantographs, e.g., using a 3D printed bracket. In one embodiment, we actuated the me handle using a small motor (Pololu, 6V) with a gear ratio of 10:1, which is easily back-drivable for user input. For the it handle, we chose a higher gear ratio of 75:1 to provide enough force for system output. Other motors and gear ratios are possible as well. Some embodiments may chose a low-slack transmission for higher precision, even though avoiding slack here is less crucial than avoiding slack in the 2D pantograph mechanism. Some embodiments may chose a mechanism rotating motor input by 90 degrees (e.g., bevel gears, etc.) in order to allow the length of the motors to better accommodate the shape of the linkages.

Figure 10:
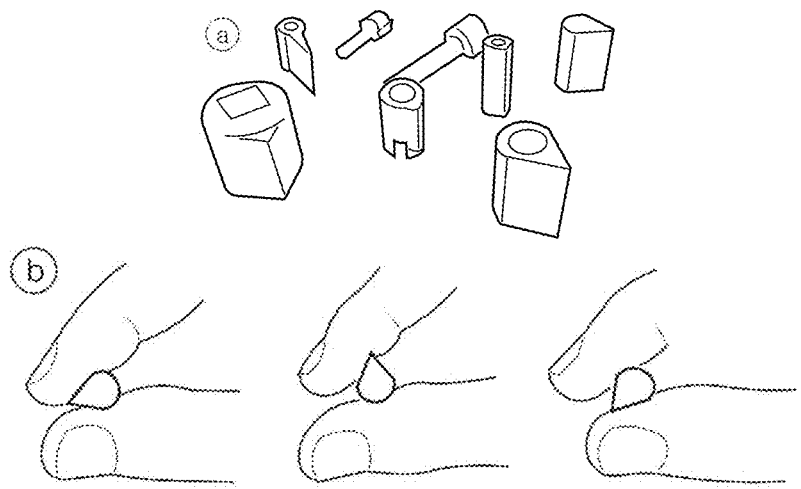
FIG. 10a is a diagram illustrating tips of handles of a haptic device according to some embodiments.
FIG. 10b is a diagram illustrating a flattened teardrop shaped tip being held between a finger and thumb in various positions according to one embodiment. (a) Selection of 3D printed handles/end effectors. (b) During use, the "flattened teardrop" design conveys the orientation of the represented me or it to the user by means of touch.
Figure 11:
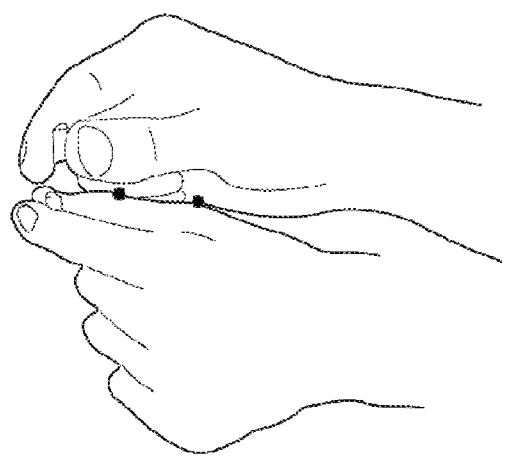
FIG. 11 is a diagram illustrating user's hands to touch each other during use, which provides users positional information. Partial rendering of showing a user interacting with just the me and it handles of a DualPanto device. The proximity of me handle and it handle causes the user's hands to touch each other during use, providing users with positional information by means of proprioceptions.

To represent direction some embodiments use an asymmetric tip mounted to the handles. They may be 3D printed, milled, injection molded, cast, etc., After experimenting with several designs (FIG. 10a) the "flattened teardrop" design (8×10×15 mm) performed best, in that holding this design between index finger and thumb clearly conveys its orientation any time (FIG. 10b). Other designs are of course possible as well.

Some embodiments arrange the two pantographs so that their handles point towards each other. This allows the two handles to be so close as to allow the user's two hands to touch during operation. Some embodiments chose a pointy tip for extra precision. All this provides users with additional tactile cues that complement proprioception and improve the user's sense of registration. Other embodiments may arrange handles so as to point in the same direction or away from each other.

Linkages

In the shown embodiment the linkages are made of 3 mm laser-cut aluminum, which is rigid enough to avoid deflection, which allows maintaining the vertical distance between the two handles. Thicker linkage designs, as in the original haptic pantographs, allow for more sturdiness and thus reduced friction (and this additional precision), thus will often be preferable.

Some embodiments use individual linkages connected using axles and various types of bearings (see, for example, the design of the original pantograph). Some or all four linkages belonging to the same pantograph can also be linked using thin bendable elements (aka "flexures" "living hinges") instead. The latter allows producing the entire linkage train in a single process, e.g., using injection molding. In some embodiments each of such linkage segments may itself consist of two, three, or four sides, that are rolled up/snapped together to produce the linkage, allowing each linkage train to be injection molded in one piece and assembled by rolling up each linkage. Some embodiments may compensate for the springyness of the living hinges by adjusting the power of motors in software.

Scale and Spatial Resolution

In order to allow rendering complex virtual worlds, such as a first-person shooter level with multiple rooms, Dual-Panto offers enough "space". However, fitting many objects into a scene is actually about spatial resolution, more so than actual scale.

In order to achieve good resolution, some embodiments minimize the size of the handle and reduce slack by choosing direct drive or transmissions subject to little or no backlash and connecting linkages with precise mechanisms, as discussed earlier.

Figure 12:
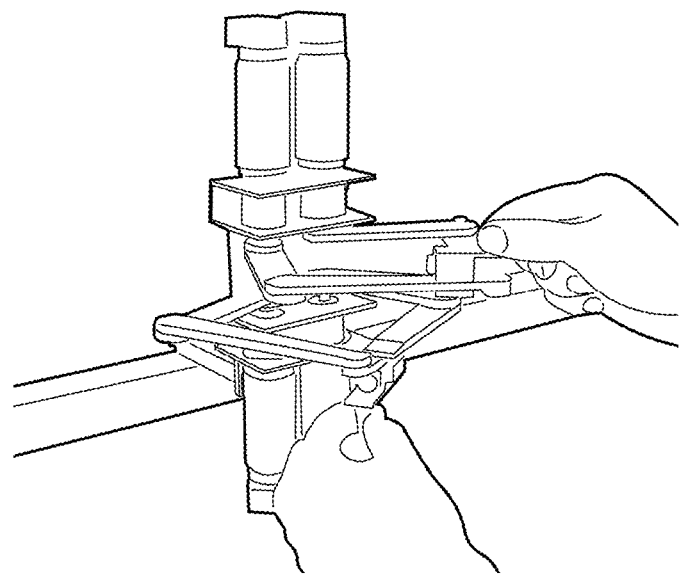
FIG. 12 is a diagram illustrating a haptic device using absolute scale according to some embodiments. Embodiment offering a larger virtual space by using longer linkages and larger motors

Larger devices with bigger motors (FIG. 12) allow offering larger absolute scale.

Software Architecture

Figure 21:
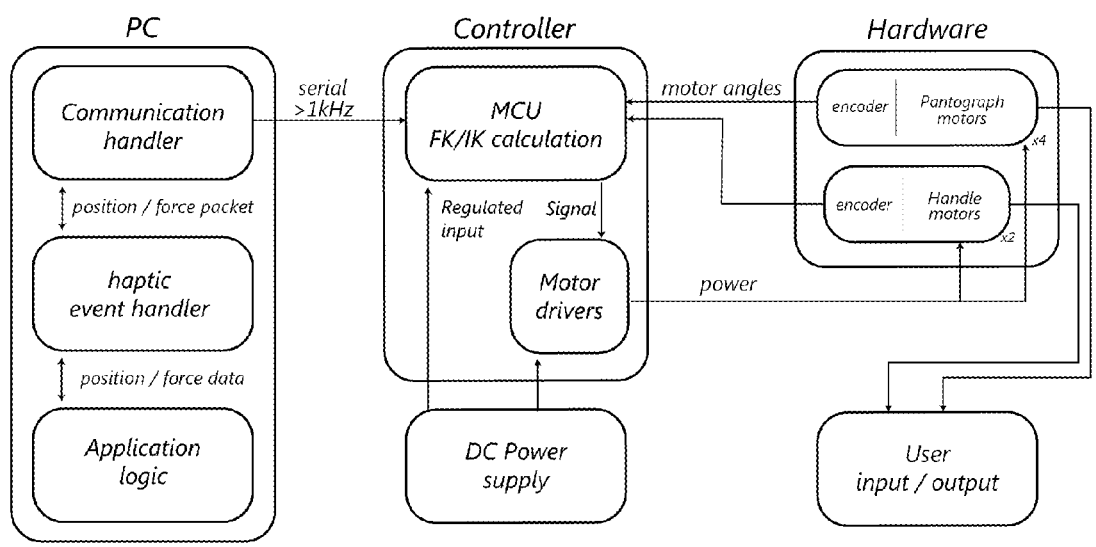
FIG. 21 is a diagram depicting the overall system hardware around the dualPanto device.

FIG. 21 shows one possible architecture that implements a dualPanto system.

The embodiment shown earlier use interfaces with the motors and encoders using an Arduino Due board and L298N motor driver. It uses native USB serial for high-speed communication to a PC (Macbook Pro). This enables it to run the haptic rendering on the computer. Our example games are implemented in Unity using the Java-based Haply framework [Colin Gallacher, Arash Mohtat, Steve Ding, and József Kövecses. 2016. Toward open-source portable haptic displays with visual-force-tactile feedback colocation. In *Haptics Symposium* (HAPTICS), pp. 65-71. DOI:https://doi.org/10.1109/HAPTICS.2016.7463157] ported and extended into C #.

The device may be driven, as a peripheral, by a personal computer, or laptop, mobile phone, tablet, smart watch or any other computing devices. The device may also integrate any of these, making it a stand-alone device.

For maximum responsiveness, some embodiments use a micro controller to run the inner control loop, i.e., to read encoder values, compare with (part of) the model/virtual world the user is currently exploring, and drive motors based on this. A processor may upload some of part of the model/virtual world geometry into the micro controller for this purpose. Other embodiments may perform this loop on the processor instead.

Haptic Rendering

DualPanto embodiments may employ four established haptic rendering techniques: (1) virtual coupling, (2) god-object constraints (3) PD control, and (4) force impulses.

Virtual coupling [J. Edward Colgate, Michael C. Stanley, and J. Michael Brown. 1995. Issues in the haptic display of tool use. In *International Conference on Intelligent Robots and Systems 95. 'Human Robot Interaction and Cooperative Robots'*, Proceedings. 1995. vol. 3, pp. 140-145. DOI: https://doi.org/10.1109/IROS.1995.525875] between the player's character and the end-effector provides resistance to the user when they try to move the me handle faster than the character can move.

DualPanto's end-effectors are implemented as custom Game Objects in Unity and coupled with god-object rendering [Yasuyoshi Yokokohji, Ralph L. Hollis, Takeo Kanade, Kazuyuki Henmi, and Tsuneo Yoshikawa. 1996. Toward machine mediated training of motor skills. Skill transfer from human to human via virtual environment. In *5th IEEE International Workshop on Robot and Human Communication*. pp. 32-37. DOI: https://doi.org/10.1109/ROMAN.1996.568646] to simulate constraints, e.g., (odd-shaped) walls. These end-effectors are also coupled to in-game characters in our applications.

To move handles to the desired position, we drive Dual-Panto's motors using traditional PD control loops. A second PD controller drives the rotation of the handle's knobs.

For both the me and it handles, fixed-value impulses provide feedback for collision events, such as picking up or shooting a soccer ball, being hit by a zombie, or a zombie being hit by a shot.

Initialization

Depending on the nature of the encoders, the device may have to be initialized once or every time it is started, or may be done whenever it is necessary. Embodiments with relative encoders (manual placement in a default position, typically such that the two handles are registered. Or run device into a stop to determine its position). Embodiments with absolute encoders may have to be calibrated only once or never.

Audio Rendering

Beside the haptic information from DualPanto, some embodiments use audio cues to provide additional information to the players during the game.

In the first-person shooter, for example, one of our embodiments provides audio cues for footsteps for both player and zombies, gunshots, hits on a zombie (reinforced with haptic impulses on the it handle), and zombie attacks on the player (reinforced with haptic impulses on the me handle).

In soccer, one of our embodiments provides audio cues for discrete changes in the game state: a user picking up the ball or shooting it, scoring a goal, and the ball reset to the center field. When a user holds the ball, "one" or "two" is spoken repeatedly to keep users aware of who has the ball.

Other embodiments may offer spatialized audio, e.g., to inform users about the position of additional its, such as enemies in a game not currently represented by the it handle.

Additional Embodiments

So far, we mostly talked about (1) two (2) pantograph units combined with (3) rotary knobs being employed to represent (4) the user's avatar me and (5) an object or opponent it. However, there are alternative ways of constructing the device and mapping information to its handles.

Alternative Handle Mappings

So far, we talked about a very particular mapping, i.e., mapping one haptic device to the user's avatar me and the other to a moving object or opponent it. However, other mappings are covered by the invention as well.

Multi-it: For example, when spectating a game, users do no possess their own avatar, so there is nothing to be represented by me. In such a mode, all handles may instead operate in it mode, allowing a user to track multiple objects, such as two players in the virtual world, one player and one projectile, two balls, etc.

Also, during a session were players have an avatar, they may still choose to set both handles to it mode, allowing a user to track two objects, such as two players in the virtual world, or one player and one projectile, two projectiles, etc.

Multi-me: In games where players control multiple avatars, such as a combat or sports team, multiple mes can be mapped to the handles.

For a given application, there will typically be different possible mappings. For example, the it handle may be mapped to the ball at all times while the me multiplexes between the players who are about to play the ball. Alternatively, the receiving and playing of the ball by me broken into two separate phases, allowing the two handles to represent two players most of the time, such as the two members on the user's team, one player each, or two players on the opponent team.

So far, we have talked about dedicated me and it handles. At any time, either the me or the it handle can switch modes. For example, during an in-game cut scene, a me handles might operate like an it handle temporarily to guide the user. Similarly, an it handle might temporarily become controllable, for example, due to a power-up in a game. This might be initiated by the system or by the player.

And, finally, some embodiments may use the devices' handles in any other way the application requires.

Embodiments with a Single Handles

So far, we have talked about devices with at least two handles and this setup allows conveying spatial information through the spatial relationship between the two handles. However, some embodiments use a single handle only, yet are still capable of conveying information useful enough to allow for meaningful applications.

First, a single handle device can represent an object that (potentially) moves over time, thus forming an it handle. Holding on to the it handle allows the user to track the represented virtual object. This, for example, allows spectating on a cyber-athletic event, where the user can now track a player through space over time. It can also be used to implement monitoring applications, or games in which users monitor and react to a moving object.

Note how this is different from motion guidance (Yasuyoshi Yokokohji, Ralph L. Hollis, Takeo Kanade, Kazuyuki Henmi, and Tsuneo Yoshikawa. 1996. Toward machine mediated training of motor skills. Skill transfer from human to human via virtual environment. In 5*th IEEE International Workshop on Robot and Human Communication.* pp. 32-37. DOI: https://doi.org/10.1109/RO-MAN.1996.568646). Motion guidance demonstrates a recorded trajectory to a user, e.g., in order to teach the movement to the user. In contrast, it handles allow users to monitor a (possibly moving) object, typically in real-time.

Second, a single handle device can represent multiple objects by means of time multiplexing. A single it handle may inform users about housing options on a city map, e.g., in combination with audio output, such as "You are currently paying 300 Euros per night" [handle moves] "at the Eurostars Hotel in Downtown Berlin. You can have the same quality standards for 240 Euros," [handle moves], "200 Euros," [handle moves] "and 320 Euros" [handle moves]. Even though the device uses only a single handle, it still conveys the relative position between objects by time multiplexing.

Obviously, time multiplexing clashes with moving object. The concept of strafing in a first person shooter game, for example, largely relies on the simultaneous perception of both avatar and opponent. On a single handle device (time multiplexing between me and it) this can still be implemented, but obviously will limit how well users can perform.

Embodiments with More Than Two Handles

So far, we talked about a device largely consisting of two haptic units. However, numbers larger than two are covered by the invention as well. In the following, we point out a few example cases, but any combination, extension, or reduction of these examples is also part of the invention.

Figure 13:
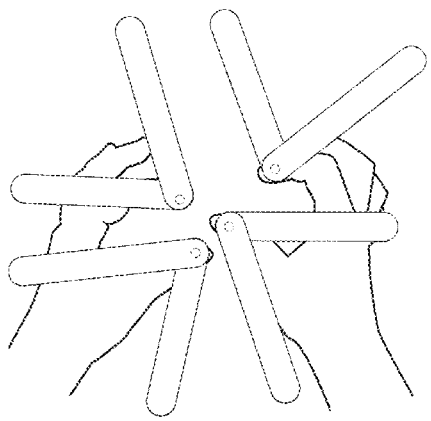
FIG. 13 is a diagram illustrating haptic devices attached to fingertips according to one embodiment. Partial rendering on an embodiment with four haptic devices.

FIG. 13 shows a setup with four handles, which allows users to sense and control four avatars, opponents, or other objects without requiring multiplexing (and more of them using multiplexing). Note that the drawing is simplified in the interest of visual clarity: first, each of the four haptic pantograph devices is reduced to the two linkages connected to the handle. Second, each of the user's fingers is connected to one haptic pantograph device with the help of a strap—these straps are not visible here.

This embodiment enables, for example, two-on-two gaming experiences. In order to allow playing tennis doubles, for example, the particular embodiment shown in FIG. 13 is arranged so that two fingers represent the user's team and two represent the opposing team. One way of doing this is using a playfield oriented right-to-left. In this situation, the user's right thumb actuates the user's left me; the user's right index finger actuates the right me. The it team=left hand playing towards the right: thumb=one player, index finger=other player. (Note that other mappings are possible as well, e.g., both thumbs forming the me team playing away from the user, while the user's two index fingers form the opposing team, playing towards the user, and so on).

The first challenge is to make the handles stay in physical contact with the respective finger or thumb at all times. There are many ways of achieving this, such as spring loading the handles to make them always push against the respective finger. Another approach is to use slings that hold one finger each, etc.

The second challenge is to allow each finger to sense the orientation of the handle (assuming the application requires this). One way to achieve this is to add additional tactile features to the knob. For example, in addition to a dedicated nose in the front, such embodiments may add an additional tactile feature, e.g., on the "back of the represented avatar's head". By making this feature clearly distinct from the nose (e.g., a set of spikes, etc.), users can tell front from back.

The third challenge is to allow the user's finger to rotate the respective knob. One approach to achieving this to let the user's finger rub the knob the way the rack "rubs" the rack in a rack-and-pinion mechanism.

As shown in FIG. 13, another embodiment achieves the three challenges by attaching each handle to the respective finger, e.g., using a loop or finger that the respective finger slides into. This allows users to actuate knobs by pointing their fingers. This leverages the user's proprioceptive sense as a means to sense the knob's orientation. While this tends to limit the range of possible rotations, for some applications this can be acceptable, e.g., ball games where players primarily try to pass and shoot forwards.

Note how this particular embodiment places all four handles in the same plane (as the four tennis players tend to largely stay in their parts of the court), but we can achieve overlapping player spaces by arranging handles in planes, as discussed earlier.

Embodiments with Even More Handles

Figure 14:
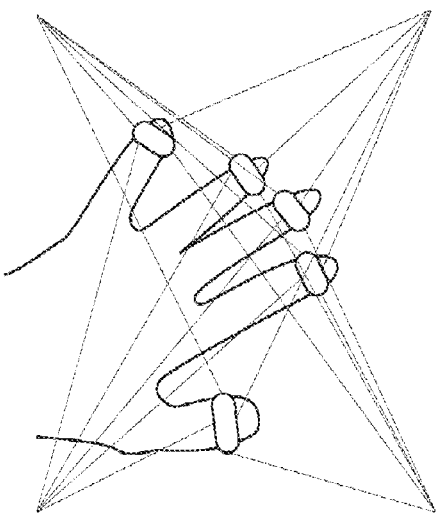
FIG. 14 is a diagram illustrating a haptics device using space interface device for artificial reality according to one embodiment. A five-finger-per-hand arrangement implemented using a SPIDAR mechanism.

Other embodiments allow users to play with more than two fingers per hand. FIG. 14 shows an embodiment that allows users to play with all five fingers per hand. This one is implemented using SPIDAR-like mechanics (Buoguila, L., Cai, Y., & Sato, M. (1997). New haptic device for human scale virtual environment Scaleable-SPIDAR. In *ICAT* (Vol. 97, pp. 93-98)). Each finger is connected to motors/encoders by means of mechanical cables, here four of them per finger. Each corner holds five DC motors (essentially winches, left out in the interest of visual clarity) capable of pulling the respective cable. This setup limits each finger's ability to move even further and makes it implement handle rotation, but it can work for applications where a limited range of motion is acceptable or where all entities assigned to one hand tend to move in concert, such as when simulating a game of rugby where players tend to stay in their "column" and pass the ball sideways.

It can also work for applications with little movement, such as a way to display five house locations in a real-estate application, etc., where the application can determine a reasonably ergonomic mapping to the fingers upfront.

While we often used the terms "game" and "play" throughout the disclosure, all description equally applies to other types of applications, such as application programs that allow users to inspect and understand data, or create spatial designs.

Co-Planar Arrangements

We can prevent haptic devices (and their handles) from colliding with each other. In the first section of this disclosure, we achieved this by placing each haptic device in a separate layer.

However, there are other ways to achieve this, as we already saw in FIG. 14.

Figure 15:
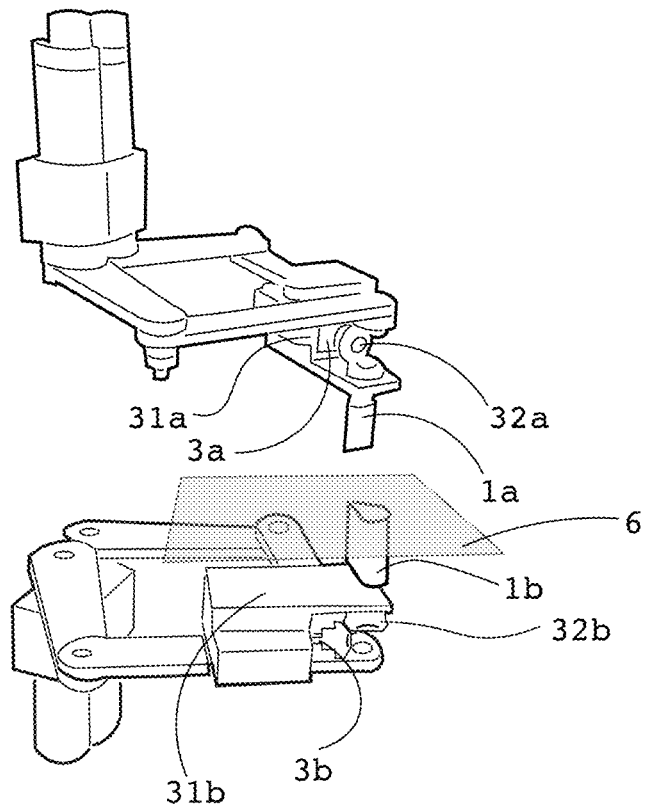
FIG. 15 is a diagram illustrating a haptic device including an it handle and a me handle in the same plane according to one embodiment. Dual pantograph configures so as to place the two handles 1a, 1b in the same layer 6, so that they will physically collide when moved to the same virtual location.

FIG. 15 illustrates yet another group of embodiments, i.e., devices that keep their haptic mechanisms in separate planes, yet place the handles in the same plane. This still keeps the haptic devices from colliding, but it allows the handles (and the user's hands) to collide. For many applications this is acceptable or even desirable though, as a collision of the physical handles might produce a sensation that adequately underlines the collision of the two virtual objects.

As already mentioned, haptic devices can be placed in the same layer if collisions are prevented in other ways, such as with application logic. For example, if two sports teams are separated by a net, as in volleyball or tennis, the haptic devices can often be arranged in the same layer. Other applications may not conceptually have such a limitation, but may introduce such constraints on the virtual in order to prevent collisions in the physical. Alternatively, an application may simply allow the physical collisions to happen.

Additional Choices for Haptic Devices in 2D

So far, we talked about haptic pantographs as the means to keep handles in their layer and to provide haptic feedback. However, there are many other devices that can be used to be implement this invention.

One, both, or all pantographs can generally be replaced by any other haptic device that offers 2 or more degrees of freedom.

For example, instead of using the two "arms" (aka linkages) of a pantograph, each haptic device may be based on a single "arm" instead, such as some sort of robotic arm. In the simplest configuration this might be a device with two servomotors arranged to rotate around a vertical axis (i.e., to perform a "yaw" rotation), but an arbitrary number of other configurations is possible as well, including arms with additional degrees of freedom, sliding mechanisms, telescoping mechanisms, and so on. Such devices may feature motors close to the respective joints or gathered at some base, transmitting forces, e.g., using cables, etc. (e.g., Phanton Force feedback device)

Another family of embodiments is based on haptic devices based on mechanical cables that pull a handle around, such as SPIDAR devices in 2D (e.g., such with 3-4 motors: Buoguila, L., Cai, Y., & Sato, M. (1997). New haptic device for human scale virtual environment Scaleable-SPIDAR. In ICAT (Vol. 97, pp. 93-98)) as well as versions that allow for yaw rotation as well. These devices can also be overlaid onto a screen(e.g., a visual screen for sighed people, or a tactile display for blind users). They can be applied with a wide range of end effectors, such as handles, rings, etc.

Another family of embodiments uses completely separate haptic devices for the two hands, i.e., arrangement without mechanical link between the two hands. This can, for example, be achieved by using a haptic exoskeleton or glove (e.g., Gu, X., Zhang, Y., Sun, W., Bian, Y., Zhou, D., & Kristensson, P. O. (2016, May). Dexmo: An inexpensive and lightweight mechanical exoskeleton for motion capture and force feedback in VR. In Proceedings of the 2016 CHI Conference on Human Factors in Computing Systems (pp. 1991-1995). ACM.). Instead such embodiments achieve registration by means of tracking each hand (e.g., using an optical, magnetic, mechanical, inertial, etc. or hybrid tracking system) and actuating each haptic glove according to its current position in space. Similar embodiments can be created using electrical muscle stimulation.

Finally, some embodiments offer just a subset of the capabilities described throughout this disclosure. For example, an embodiment may offer only one device with haptic capabilities, e.g., for the it handle, while the me handle is input only and does not allow providing force feedback.

Additional Choices for the Haptic Handles

Figure 16:
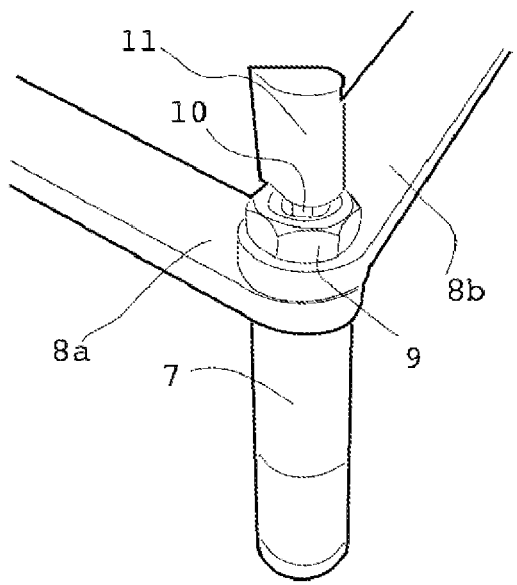
FIG. 16 is a diagram illustrating a handle motor according to one embodiment. This shows an alternative way to mount a handle motor. A geared motor with encoder 7 is directly mounted on a linkages 8a, 8b, and its shaft 10 goes through nut 9 then a handle 11 is mounted on a top.
Figure 17:
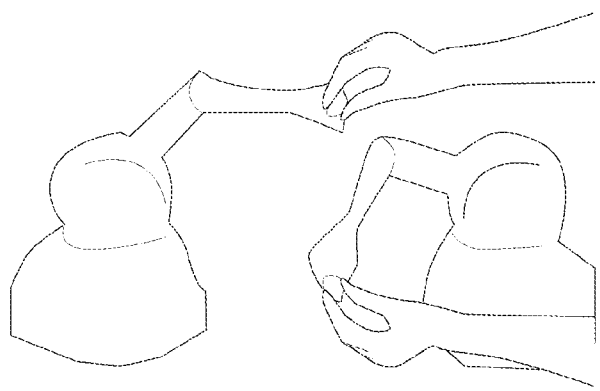
FIG. 17 is a diagram illustrating an example embodiment based on two 3D haptic devices. Each device may offer between 3 degrees of freedom (end effector moves in 3D) and 6 degrees of freedom (end effector can also be rotated and/or tilted and rolled)

In the design shown earlier, we used bevel gears to transmit movement from a motor (with encoder) to the handle. This does not have to be so. As someone skilled in the art will appreciate, there are many ways how to mount the motors to obtain the desired movement. For example, as shown in FIG. 16, the respective motor could instead be mounted perpendicular to the linkages, such that motor axle also implements the axle holding the linkages together. In the shown example, the motor, could for example, be rigidly connected to linkage B. Note that motor, gearbox, and encoder can be placed in many different arrangements and permutations.

Handles do not have to be actuated by a rotary motor either; alternatives include any type of rotary actuator, as well as properly mounted linear actuators, etc.

Encoders can be any type, including absolute and relative encoders, optical and magnetic, and so on.

Placement of Handles

In the shown design, we had handles pointing towards each other, as this allowed us to get the handles into the closest possible proximity. As discussed earlier, other embodiments, however, may have the handles pointing away from each other, pointing in the same direction, etc. as this can, for example, allow for a more compact form factor, e.g., for mobile use.

Embodiments that Support 2½D or 3D Interaction

So far, we talked about haptic devices moving in 2D. However, there are many haptic devices that allow for movement in 3D; some of them also support up to 3 degree of freedom of rotation, such as translations along three axes (e.g., Novith Falcon) or even additional axes of rotation, such as roll, pitch, and yaw, for an overall number of six degrees of freedom (e.g., Geomagic Phantom Premium 6DoF, http://www.geomagic.com/en/products/phantom-premium/overview). This includes devices already designed for use in haptics, such as phantom 3DOF and 6DOF devices, or any other device in this line of engineering, as well as devices based on mechanical cables, such as 3D versions of SPIDAR.

Figure 18:
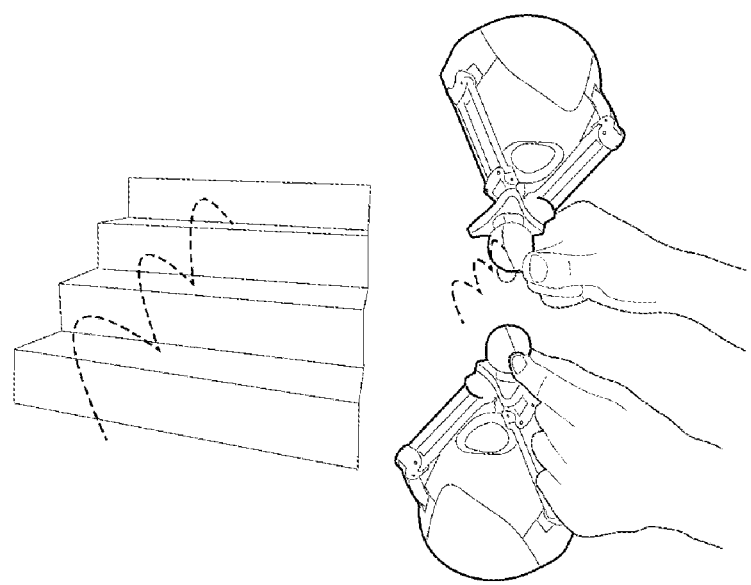
FIG. 18 is a diagram illustrating three-dimensional interaction using a 3DoF haptic device, which allows users sense change in altitude. Example embodiment based on two 3 degree of freedom haptic devices (such as Novinth Falcon). When the user's avatar walks down virtual stairs (left) the device's me handle follows the movement in 3D.

Such devices allow implementing the instant invention in 3D. A device created by stacking one 3D force feedback device (e.g., Novinth Falcon or similar) with the handle facing down on top of another 3D force feedback device (e.g., Novinth Falcon or similar) with the handle facing up, for example, allows users to explore a 2½ and to a certain extent 3D world, such as a game in which they can walk up and down stairs and actually feel the change in altitude, as shown in FIG. 18. These designs may still be complemented with a rotatable handle as discussed earlier or with a handle that can rotate along additional axes.

2½D and 3D devices are a straightforward extension of what we discussed above, but are subject to two additional challenges.

First, they are more prone to collisions between haptic devices and their handles. This makes robotic arms attractive as a means for implementing the haptic device, as they involve only a single arm for handle, which brings less clutter into the space. Someone of skill in the arts would appreciate that collision avoidance can often be resolved by means of robotic motion planning. This can, for example, be accomplished with additional degrees of freedom, for example 4 or more DoF robot arms, giving the system additional choices when trying to avoid collisions.

Regardless of the DoF of the robot arms, such devices could be grounded either to the environment, such as mounted to a table or the floor, or to the user themselves as an exoskeleton.

Second, the user's comprehension of registration is less obvious. In 2D, our general concept was to define two handles as collocated if a defined global projection function projects one onto the other. In 3D, projection is not really an option, as projection eliminates a dimension, so at least one of the degrees of freedom of the device would become meaningless. Thus collocation has to mean actual collocation, i.e., (e.g., by using a long pointy tip or similar) two handles will refer to the same location if and only if these tips are actually collocated.

Other embodiments resolve physical collisions by employing techniques known from off-screen visualization techniques, i.e., refer to a point outside the device itself. Two handles may be considered collocated if they are in the same position after applying an predefined constant offset (which draws inspiration from "offset cursor", Potter and Shneiderman 1988), by pointing to it using an incomplete tangible (2D or 3D) arrow (Gustafson et al. Wedge: Clutter-Free Visualization of Off-Screen Locations, 2008) an incomplete tangible circle or sphere (Baudisch & Rosenholtz, Halo, 2003), etc.

Some embodiments combine 3D haptic devices with 2D haptic devices. Any such combination is encompassed by the invention as long as there is a global mapping that allows determining whether or not the two devices are referring to the same location.

Registration by Projection

So far, we talked about haptic devices that achieved registration by means of a global projection function that projected the handle of one device vertically on the other device. Other embodiments may use other projection functions, such as projects, but not limited to, affine transformations, homographies, etc. Yet other embodiments may use mappings that go beyond projections, e.g., by including distortions, such as a fisheye effect or such.

Interaction Planes

So far, we talked about 2D haptic devices that allowed for movement in a horizontal plane. This does not have to be the case. The device may be oriented for the interaction to take place in other planes, such as sideways and up-and-down from the user's perspective, e.g., for side-scroller games and other applications that use this plane, such as generic screen interfaces. The device may also be operated in a vertical plane that allows for up/down and in/out movement from the user's perspective—or any other plane.

Some embodiments allow the device to be mounted in different ways, offer a hinge or gimbal or ball joint or the such to pivot the device into the desired position.

Alternative Devices

Haptic Device on Tactile Display

To far, we talked about a registered combination of a force feedback device (such as the pantograph) with another such devices. However, other combinations are possible and in particular, it is possible to combine one (or more) force feedback devices with tactile devices, i.e., devices that produce a surface or frame of similar that produces a sensation conveying shape or texture to the human skin when touched. As before, the registration between the two is key, i.e., an element in the virtual world displayed on the tactile display and another collocated element in the virtual world should be positioned, such that some global projection maps one onto the other.

Some embodiment may combine the device as discussed so far with a physical frame that users can feel during operation. This frame may, for example, be rectangular in order to represent the boundaries of a rectangular virtual world, such as a soccer stadium in which the interaction takes place, or a rectangular document, etc. It could have any shape and represent any stationary elements of the virtual world though or its shape could even be adjustable or self-adjusting, allowing it to change what is represented. Even (and especially) when static, such a frame or similar can serve as spatial reference, allowing users to understand where they are located within the virtual world, such as "Close to the North West corner" or "close to the corner of the opponents goal" in a soccer game. It can also allow users to revisit a location efficiently, by tracking their path back to that same corner based on the tactile sensation delivered by the frame.

Figure 19:
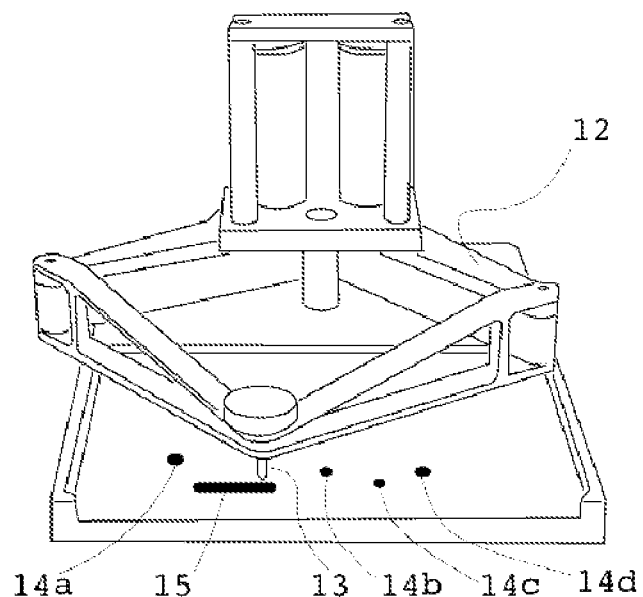
FIG. 19 is a diagram illustrating a single pantograph and a tactile display according to one embodiment. Embodiment consisting of a single pantograph 12 combined with tactile display 13, below¬ that holds four tactile dots 14a, 14b, 14c, 14d and a tactile line 15.
Figure 20:
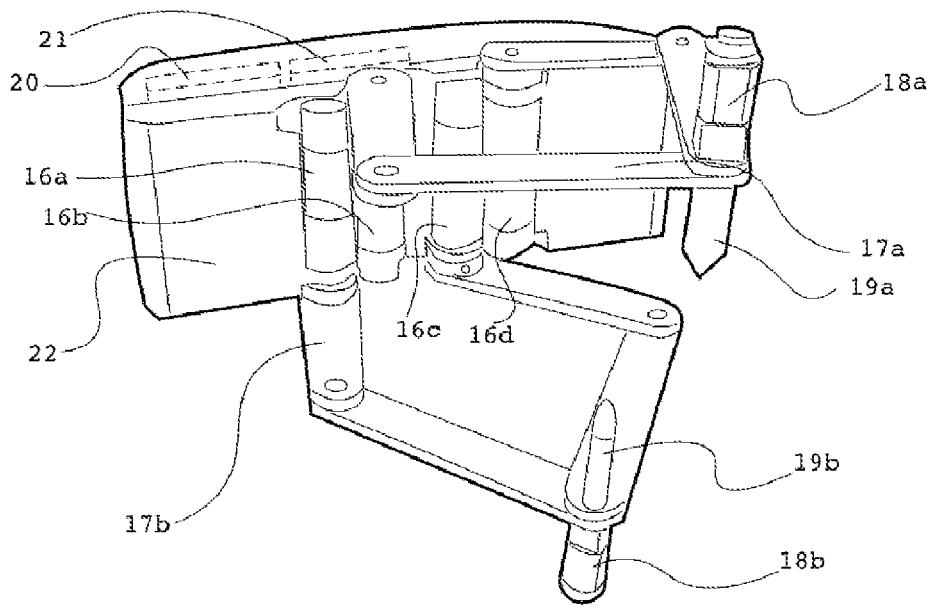
FIG. 20 is a diagram depicting one possible mobile embodiment. One possible mobile embodiment. Two pantographs 17a, 17b are connected through pantograph motors 16a, 16b, 16c, 16d, which is alternately fixed to a casing 22. Handle motors 18a, 18b are directly mounted on the pantographs 17a, 17b, connected to me/it handles 19a, 19b. A driver boards 20 and batteries 21 can be stowed in a casing 22.

A similar effect can be achieved using a tactile surface, located e.g., located below the area actuated using the force feedback devices (FIG. 19). Such a tactile surfaces may be largely flat (such as paper or cardboard, swell paper) or with pronounced 3D features (e.g., 3D print); it may be static, dynamic, or animated (e.g., Braille displays or a Braille array, such as the Hyperbraille 60×120 pin Braille array, or similar).

Embodiments may combine one or more tactile displays with one or more haptic force feedback devices.

Hand Use/Foot Use/Etc.

So far, we talked about haptic devices operated by hand and a single trigger button operated by foot. This does not have to be this way.

First, instead of a single trigger button there may be zero or multiple such buttons. Second, any other type of input hardware maybe added, such as sliders, touch pads, gesture sensors, cameras, speakers, and so on.

Second, any hardware, including the haptic devices and the button(s) currently implemented as footswitches, may be operated by foot, by hand, or any other limp, such as knee, elbow, tongue, gaze, etc. In particular, such switches, buttons, and sliders may be placed at the end effector/handle or along the linkages, where users can reach them easily.

All embodiments may also be combined with sound input and/or output (speakers, speech as sound recognizers, etc.), as well as speech input and/or output. Especially when both hands are occupied operating two haptic devices, users may use speech recognition to issue commands, trigger weapons and so on.

Speech output may be used to complement the recognition of the scene, e.g. by providing a survey of the document, passage, world, room, location, etc. the user is currently interacting with. A user entering a room may or a user asking for it may, for example, receive a quick survey of the locality that is either just audio output or combines audio output with haptic output, such as "following the pathway (it handle moves along the pathway) "kill the guard . . . " (it handle emphasizes the position of the guard standing on the pathway, e.g., by wiggeling, etc. " . . . and the moster" (same for the moster) "before existing this room through a door located in the North-East corner" (it handle reaches the door).

Spatialized sound and/or spatialized speech may, for example, be used to provide users with awareness of additional objects in the virtual world, such as additional opponents, power-ups, etc. in the case of a shooter game, thereby serving as an alternative or additional support for what we presented as multiplexing.

Modular Embodiments

Some embodiments may be modular in nature, allowing additional haptic units of various types to be added, e.g., at runtime.

The invention as Stand-Alone Device, Peripheral, etc.

Some embodiments may be designed to allow for stand-alone use. Similar to a mobile gaming console, such as a Gameboy, Nintendo DS, iPod Touch, iPad, Android phone, or such, such embodiments tend to feature a more complete set of hardware, such as microprocessor or microcontroller, their own RAM and persistent storage, motor driver, optional speech generation, optional speech recognition, one or more microphones and speakers, optional batteries, and so on. Such devices may also be designed to allow for quasi instantaneous start-up, e.g., by using ROM-like storage or by offering a hibernation mode.

In contrast, other embodiments may be designed to primarily complement a computing device, such as game console, touch device, mobile tablet, mobile phone, VR device, laptop or other personal computer, etc. Such embodiments may offload some or a lot of the required hardware to the computing device. In the most extreme case, the presented device simply forms a peripheral that is plugged into a computing device in a way where the computing device runs the application, the device driver, provides power, runs sound and speech generation and recognition, and so on.

The space between stand-alone console and peripheral is a continuum with many useful configurations in between. Just to name a few, an embodiment may be capable of operating stand-alone, but may still allow connecting to a computing device in order to offer enhanced functionality, such as any or all of these: (1) sound and speech input and output or just a better speaker, (2) more processing power, (3) a screen that allows sighted users to spectate (multiple such devices can connect), (4) allow connecting to the LAN, Wi-Fi, or Internet, (5) allow connecting to a server for firmware updates, (6) connecting to an app store to load additional apps, (7) connecting to a server or store or similar to upload contents created on the device, (8) allow connecting to other instances of the present invention in order to allow for multi-user application use (such as Google docs) or multiplayer gaming or as spectators.

Embodiment may connect to a computing device by means of a wired connection or wirelessly using, for example, Wi-Fi, Bluetooth, Any type of radio signal transmission device, optical coupling, etc.

Mobile Embodiments

Some embodiments are designed specifically for mobility, e.g., by featuring a battery-based power supply instead of or in addition to an AC adapter.

In order to achieve compactness, mobile embodiments may allow folding up linkages into a largely collinear arrangement, so as to save space. For example, allowing a rotation or twisting movement to align motors with linkages, so as make the resulting arrangement more compact. Other embodiments may arrange motors so as to be largely parallel to the linkages, again allowing for denser packing.

While the embodiments shown earlier were mounted to a tripod, other embodiments including those intended for mobile use may contain both pantographs in a single casing, to attach to the environment using other means, such as suction cups, clamps, magnets, wire, strap, etc. or may even be operated hand-held.

Connection to Sighted Users and Spectating

So far, we talked primarily about the experience of blind users using the device. However, some embodiments may connect the device to additional copies of the same or similar embodiments, allowing multiple blind users to collaborate or compete. In such setups, the experience may run on any of the devices, on multiple of them, or on a dedicated server.

Similarly, a system may allow interfaces and devices for sighted users to explore or interact with the virtual document or space explored or interacted with using the present invention. If at least one user wants to interact based on sight, the system needs to generate graphics; this may again happen either locally or on a server, etc.

If an application is intended for blind use exclusively, visual graphics, such as textures may never have to be created and stored in the first place. However, if sighted users are considered, the experience might, for example, be designed based on visual graphics in the first place.

Multi-User Systems

So far, we have discussed either one- or two-user systems. However, two or more users can use systems connected either locally or through a network using, for example, a client-server system or a cloud-based game lobby. Users could, for example, host a game or other application for several other users for a multi-user game or application. This could occur locally on a single device or hosted computer, through a local network, or connecting several users who are not physically collocated by connecting through the Internet.

Eco System

The ecosystem around the device may contain additional software and hardware elements.

An app store may allow users to download additional apps. Users may operate the app store as they already do on today's mobile phones (e.g., using touch combined with speech input and output) or the app store may itself use the instant invention to enhance its capabilities, e.g., by placing apps in a virtual space that users can browse using the device, to use the embodiment to provide previews of apps, etc.

Some embodiments will offer a software library that implements an application programmer interface (API) that allows applications to access the device functionality in an efficient way. Applications for use with the instant invention may then be written, stored, and shared in a format in a way that makes use of this API.

While we talked so far about an eco system largely targeted at users consuming experiences, the eco system may also offer tools that allow users to create their own contents. A level editor for first person shooters, for example, may allow users to create levels by placing rooms and walls, extending walls, placing opponents, demonstrating how opponents move and attack, etc.

Experience design may be supported with the help of a game engine and/or asset store.

Non-Gaming Applications

While we talked mostly about interactive games, the present invention may be used for a wide range of applications, including those that are not games and including applications that do not contain moving objects (such as the applications shown in "Saiganesh Swaminathan, Thijs Roumen, Robert Kovacs, David Stangl, Stefanie Mueller, and Patrick Baudisch. Linespace: A Sensemaking Platform for the Blind. In Proceedings of CHI 2014", which is incorporated by reference herein in its entirety). The present invention will still often be useful for such applications, because the it handle allows the application to point users to locations and to show them one-dimensional objects, such as streets, rivers, the walls of a room, etc.

To illustrate this, we use the example of a home finding app. A user may, for example, ask "show me three bedroom condos for under $500,000" and the system might reply by saying "I found 4: here, here, here, and here" and every time move the it handle to the respective location.

The user may then "hold on" to one of the condos by moving the me-handle there (the me handle may simplify this by snapping to the locations just listed). Worried about noise, ask "how close is this to the train tracks". The system may not only respond by saying "The condo is 220 meters from the train tracks", but also guide the user's hand using the it handle along the trans tracks, optionally pointing out train stations with tactile icons.

Figure 22:
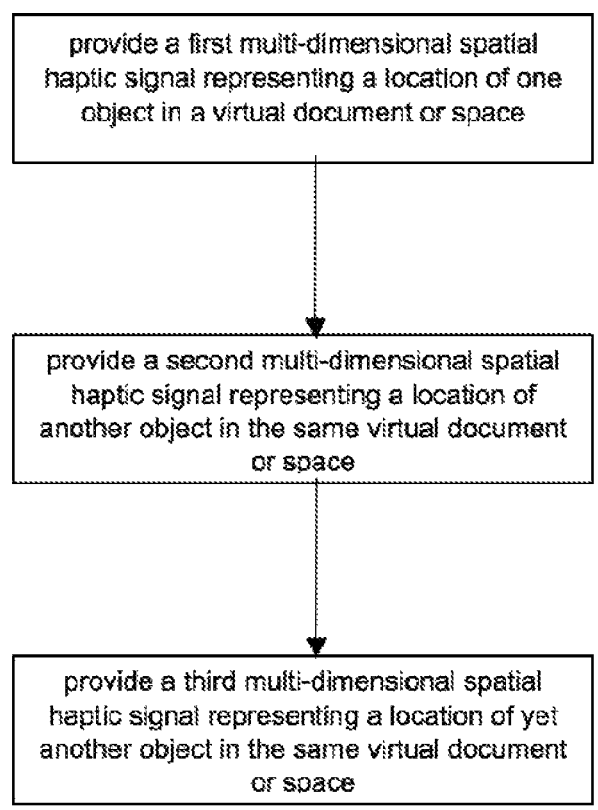
FIG. 22 is a flowchart illustrating a process flow of operation of a haptic device according to one embodiment.

FIG. 22 is a flowchart illustrating a process flow of operation of a haptic device according to one embodiment. The haptic device provides a first spatial haptic signal representing a location of one object in a virtual document or space. The end handle of a first (e.g., a me handle of a first haptic device) may provide the first spatial haptic signal. The haptic device provides a second spatial haptic signal representing a location of another object in the same virtual document or space. The end handle of a second handle (e.g., an it handle of a second haptic device) may provide the second multi-dimensional spatial haptic signal. The end handles of the it handle and the me handle and the signals thereof are spatially registered with respect to each other.

In some embodiments, the second multi-dimensional spatial haptic signals indicate haptic feedback. In some embodiments, the haptic device provides force feedback to allow users to feel virtual objects in the virtual space. In some embodiments, the object represented by the first haptic device is a user's avatar. In some embodiments, the user can move around in the virtual world by moving the end handle of the haptic device.

In some embodiments, the haptic device inhibits movement of the handle when the user's avatar encounters obstacles in the virtual world. In some embodiments, the handle in the second haptic device moves in response to movement of the object in the virtual world that it represents. In some embodiments, the handle of the second device traverses sequences of two or more objects in virtual space to convey the spatial relationship between these objects to the user.

In some embodiments, at least one of the first and second spatial haptic devices is a pantograph haptic device. In some embodiments, at least one of the first and second spatial haptic devices is a 3D haptic force feedback device. In some embodiments, the haptic device provides orientation of the object in virtual space, for example, via a knob of a spatial haptic device. In some embodiments, the haptic device provides a third spatial haptic signal to represent a location of yet another object in a virtual document or space.

Reference in the specification to "one embodiment", "an embodiment", "various embodiments" or "some embodiments" means that a particular feature, structure, or characteristic described in connection with these embodiments is included in at least one embodiment of the invention, and such references in various places in the specification are not necessarily all referring to the same embodiment.

All publications, patents, and patent applications cited herein are hereby incorporated by reference in their entirety for all purposes to the same extent as if each individual publication, patent, or patent application were specifically and individually indicated to be so incorporated by reference.

Some portions of the detailed description herein are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

What is claimed:

1. A haptic device comprising:
a first spatial haptic device including a first handle to represent a location of a first object in a virtual document or space independent of whether a visualization of the virtual document or space is generated; and
a second spatial haptic device including a second handle to represent a location of a second object in the same virtual space independent of whether a visualization of the virtual document or space is generated,
wherein the first and second handles are spatially registered with respect to each other.

2. The device of claim 1, wherein the first object represented by the first haptic device is an avatar of a user.

3. The device of claim 2, wherein the user can move the avatar of the user around in the virtual document or space by moving the first handle of the first haptic device.

4. The device of claim 3, wherein the first haptic device inhibits movement of the first handle when the user's avatar encounters obstacles in the virtual document or space.

5. The device of claim 1, wherein the second handle in the second haptic device moves in response to movement of the second object in the virtual document or space-independent of whether a visualization of the virtual document or space is generated.

6. The device of claim 5, wherein the second handle of the second device represents different objects in the virtual document or space at different times.

7. The device of claim 1, wherein at least one of the first and second spatial haptic devices is a pantograph haptic device.

8. The device of claim 1, wherein at least one of the first and second spatial haptic devices is a 3D haptic force feedback device.

9. The device of claim 1, wherein at least one of the first and second handles itself is a haptic device representing an orientation of that object in the virtual document or space.

10. The device of claim 1, further comprising a third spatial haptic device including a handle to represent a location of a third object in the virtual document or space independent of whether a visualization of the virtual document or space is generated.

11. A method comprising:
providing a first spatial haptic signal representing a location of a first object in a virtual document or space independent of whether a visualization of the virtual document or space is generated; and
providing a second spatial haptic signal representing a location of a second object in the same virtual document or space independent of whether a visualization of the virtual document or space is generated,
wherein the first and the second spatial haptic signals are spatially registered with respect to each other.

12. The method of claim 11, wherein the first object represented by the first haptic signal is an avatar of a user.

13. The method of claim 12, wherein the user can move around in the virtual document or space by changing the first haptic signal.

14. The method of claim 13, wherein changing the first haptic signal is inhibited when the user's avatar encounters obstacles in the virtual document or space.

15. The method of claim 13, wherein the second haptic signal changes to indicate a change in location in response to movement of the second object in the virtual document or space.

16. The method of claim 13, wherein the second haptic signal represents different objects in the virtual document or space at different times.

17. The method of claim 11, wherein at least one of the first and second spatial haptic signals is a 3D haptic force feedback signal.

18. The method of claim 11, wherein at least one of the first and second haptic signals represents an orientation of that object in virtual document or space.

19. A non-transitory computer-readable storage medium including instructions that, when executed by a processor, cause the processor to perform a process of:
providing a first spatial haptic signal representing a location of a first object in a virtual document or space independent of whether a visualization of the virtual document or space is generated; and
providing a second spatial haptic signal representing a location of a second object in the same virtual document or space independent of whether a visualization of the virtual document or space is generated,
wherein the first and the second spatial haptic signals are spatially registered with respect to each other.

20. A device comprising:
a first spatial haptic mechanism with a first handle that represents a location of a first virtual object in a virtual document or space independent of whether a visualization of the virtual document or space is generated,
wherein the first handle tracks the first virtual object over time.

21. The device of claim 20, further comprising
a second spatial haptic mechanism with a second handle that represents a location of a second virtual object in the virtual document or space independent of whether a visualization of the virtual document or space is generated,
wherein the first and the second spatial haptic mechanisms are spatially registered with respect to each other; and
wherein the second handle tracks the second virtual object over time.

22. The device of claim 20, further comprising
a second spatial haptic mechanism with a second handle that represents a location of a second virtual object in the virtual document or space,
wherein the first and the second spatial haptic mechanisms are spatially registered with respect to each other; and
wherein the second handle represents an avatar of a user.

23. The device of claim 20, wherein the first spatial haptic mechanism is a pantograph haptic device.

24. The device of claim 5,
wherein the location or orientation of the second object changes over time in response to an external computing system,
wherein the second handle provides a haptic signal to continuously convey the changing location or orientation as a sensed location or orientation to a user.

25. The device of claim 5,
wherein the first object originates from a first user;
wherein the second object originates from a second user that is not the first user,
wherein the location or orientation of the second object changes over time in response to input from the second user,
wherein the second handle provides a haptic signal to continuously convey the changing location or orientation as a sensed location or orientation to the user.

* * * * *